United States Patent
Sibeijn et al.

(10) Patent No.: US 6,268,186 B1
(45) Date of Patent: Jul. 31, 2001

(54) HMG-COA REDUCTASE INHIBITOR PREPARATION PROCESS

(75) Inventors: Mieke Sibeijn, Av Amersfoort; Aad Johannes Bouman, Pl Rotterdam; Robertus Mattheus De Pater, Zl Delft; Cornelis Frederik Purmer, De Delft, all of (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 09/423,370

(22) PCT Filed: May 4, 1998

(86) PCT No.: PCT/EP98/02616

§ 371 Date: Jan. 12, 2000

§ 102(e) Date: Jan. 12, 2000

(87) PCT Pub. No.: WO98/50572

PCT Pub. Date: Nov. 12, 1998

(30) Foreign Application Priority Data

May 8, 1997 (EP) .................................................. 97303111

(51) Int. Cl.[7] .............................. C12P 17/06; C12P 7/62; C07C 69/732; C07C 67/317
(52) U.S. Cl. .......................... 435/125; 514/451; 514/460; 549/271; 549/292
(58) Field of Search ........................... 435/125; 549/292, 549/271, 451, 460; 560/119, 256

(56) References Cited

U.S. PATENT DOCUMENTS

Re. 36,520 * 1/2000 Smith et al. ...................... 514/548
4,231,938    11/1980  Monaghan et al. .
5,403,728 *  4/1995  Jekkel et al. .......................... 435/125
5,712,130 *  1/1998  Hajko et al. .......................... 435/125
5,989,877 * 11/1999  Pater et al. ........................... 435/158

FOREIGN PATENT DOCUMENTS 2 077 264    12/1981  (GB) .

OTHER PUBLICATIONS

Kleinsek, D. A. et al., "Purification of 3–hydroxy–3–methylglutaryl–coenzyme A reductase from rat liver," Proc Natl Acad Sci USA (Apr. 1977) 74(4):1431–1435.

Beg, Z. H. et al. "Purification and Characterization of 3–hydroxy–3–methylglutaryl coenzyme A Reductase from Chicken Liver," FEBS Letters (Aug. 1977) 80(1):123–129.

Knauss, H. J. et al. "Biosynthesis of Mevalonic Acid from 1–C[14]–Acetate by a Rat Liver Enzyme System," *The Journal of Biological Chemistry* (Nov. 1959) 234(11):2835–2840.

* cited by examiner

*Primary Examiner*—Herbert J. Lilling
(74) *Attorney, Agent, or Firm*—Morrison & Foerster LLP

(57) ABSTRACT

The invention provides a simple and selective method for the deacylation of 4-acylated statins during the preparation of statins from a fermentation broth, more specifically a reduction of impurities from the process, by increasing the pH of the fermentation broth.

9 Claims, No Drawings

HMG-COA REDUCTASE INHIBITOR PREPARATION PROCESS

The present invention relates to a process of preparing, purifying and/or isolating compounds which are hydroxymethyl glutaryl coenzyme A (HMG-CoA) reductase inhibitors (or their precursors) such as lovastatin. The invention in particular relates to purifying such a compound from a composition comprising microorganisms that have produced it (such as by using an adsorbent resin), performing an extraction using toluene, performing a lactonization reaction, if necessary (e.g. in the toluene), and washing the toluene with water before isolating the final compound.

It is known that certain mevalonate derivatives are active as hypercholesterolemic agents, and these function by limiting cholesterol biosynthesis by inhibiting the enzyme HMG-CoA reductase. Mevalonate derivatives include the naturally occurring fungal metabolites lovastatin and compactin.

Lovastatin can be produced by fermentation of various microorganisms including *Aspergillus terreus,* during which it is produced in a free hydroxy acid form along with a number of by-products. Consequently, isolation usually involves removal of the microorganisms (usually referred to as the biomass) and by-products, followed by lactonization (to the closed ring or lactone form, called lovastatin) and removal of by-products. Several methods of isolation have been developed, but they are usually multi-step processes involving extraction from a fermentation broth (or a filtrate thereof) using organic solvents. Due to the number of steps involved the yield of lovastatin is generally low. In addition, large quantities of potentially hazardous solvents are usually required which not only entails the requisite safety measures but additionally increases costs dealing with solvent disposal.

The present invention seeks to provide a process of purifying or isolating an (3-hydroxy-3-methyl glutaryl-coenzyme A) HMG-CoA reductase inhibitor, such as lovastatin, or a precursor thereof, starting from a composition comprising cells (e.g. microorganisms) which have produced the precursor or inhibitor, in good yield and/or using reduced quantities of solvent.

In a first aspect the invention provides a process of purifying a compound, which is preferably an HMG-CoA reductase inhibitor, or a precursor thereof, of the general formula I or II:

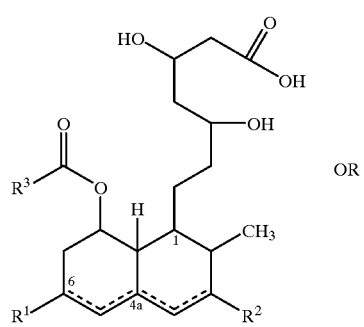

(I)

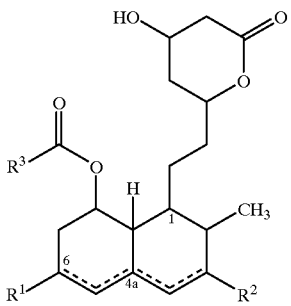

(II)

wherein:
each of $R^1$ and $R^2$ independently represents a hydrogen atom, a methyl group or a hydroxyl group; and
$R^3$ represents a (straight chain or branched) $C_{2-6}$ alkyl group;
or a salt or isomer thereof;
and there is one double bond present in the first ring, between either carbon atoms 3 and 4 or atoms 4 and 4a, and no or one double bond in the second ring, which if present is between either carbon atoms 4a and 5 or atoms 5 and 6;
from an (e.g. aqueous) composition comprising cells, such as microorganisms, that have produced the compound, the process comprising:
(a) adjusting, if necessary, the pH of the composition to be at least 7.5;
(b) removing (e.g. by filtering) from the composition the cells to obtain a solution of the compound (e.g. a filtrate);
(c) contacting the solution with a resin so that the compound is adsorbed onto the resin; and
(d) removing the compound from the resin.

By this process the compound can be absorbed onto a resin and so purified. The cells can be removed by filtration (in which case one is left with a filtrate), centrifugation (so one obtains a supernatant) or even by decantation. Whichever method is employed, the remaining cells (or biomass), or the waste liquid resulting from passage over the resin, can then be discarded, without further processing. This can be achieved because no (non-aqueous) solvent need be added to either the composition or the solution prior to contact with the resin, unlike prior art processes. The compound is suitably removed from the resin by elution.

The purification process can thus result in a concentration of the compound, and when the resin is a hydrophobic one, it is possible to remove polar components present in the original composition.

The adjustment to a pH of at least 7.5 has been found to improve purification because this assists in the dissolution of the compound. Several prior art processes, such as those described in U.S. Pat. Nos. 4,231,938 and 4,294,926 (Merck) purify the precursor (to lovastatin) from an essentially neutral fermentation-derived medium, but that is not basified, unlike the process of the present invention, and as a result not all the precursor has dissolved. Therefore, some of the precursor can remain either with the microorganisms when they are removed (by centrifugation).

A precursor is a compound that can be converted into the reductase inhibitor by a relatively simple or straightforward chemical conversion, such reactions being known in the art. This may involve several steps, although sometimes only one reaction is required, and that is lactonization (described later in relation to the second aspect of the invention). This is the closing of the "open" ring and results in a compound of the formula II. However, many compounds of formula I are inhibitors although they are sold (and often administered) in the lactone form of formula II. These are converted to the open ring form of formula I in vivo.

Alternatively, a precursor can be converted into a reductase inhibitor by a hydroxylation reaction, such as at the 6-position, and this can be achieved by using various microorganisms, for example those described in GB-A-2,077,264 (Sankyo).

Preferred reductase inhibitors are able to inhibit the biosynthesis of cholesterol, and so can be useful as hypercholesterolemic agents. The test for HMG-CoA reductase inhibition is well known in the art, but for example one can use the methodology of Beg et al, FEBS Letters 80:123–129 (1977) or described in J. Biol. Chem. 234:2835 (1959). Suitable enzymes can be prepared as described by Kleinsek et al, PNAS 74:1431–5 (1977).

In formulae I and II, suitably $R^2$ represents a hydrogen atom. Preferably $R^3$ represents a 1-methyl propyl group (as is the case for lovastatin, pravastatin and compactin) or a 1,1-dimethyl propyl group (as is the case with simvastatin).

Preferably the compound will have one double bond in each of the first and second rings, suitably located between carbon atoms 3 and 4 and carbon atoms 4a and 5 (as is the case with lovastatin, pravastain, compactin and simvastatin, although compounds which have only one double bond, located in the first ring, are contemplated (such as between carbon atoms 3 and 4, in the case of dihydrolovastatin). Other compounds that are contemplated have a double bond in the first ring between carbon atoms 4 and 4a and a double bond in the second ring between carbon atoms 5 and 6 and are described in GB-A-2,077,264 (Sankyo)

The (usually aqueous) composition comprising the cells (usually microorganisms although plant or animal cells modified to produce the precursor can be used) can be any composition which comprises the compound of general formula I or II. It will often contain water and microorganisms, particularly when the composition comprises a fermentation broth, a sample removed from such a broth (e.g. before fermentation is complete) or a sample from the broth which has been stored, for example at a low temperature.

The microorganism can be any microorganism that is capable of producing the compound and this includes bacteria, yeasts and (preferably) fungi. Preferred microorganisms are fungal, for example of the genus Aspergillus, Monascus, Penicillium , Paecilomyces, Hypomyces, Phoma, Pleurotus, Doratmyces, Eupenicillium, Gymnoaxus and Trichoderma.

Of these, one can optimally use a fungus of the species *Penicillium citrinum* or *Aspergillus terreus,* for example strain AD43.

Preferably, in (a) the composition is adjusted to have a pH of from 9 to 13, such as from 10 to 11. The composition may be diluted with water. The pH can be adjusted by any suitable alkali. Preferably, it is an alkali metal hydroxide, for example sodium hydroxide, for example 1–3N, such as about 2N, NaOH.

At this stage in the process the composition is usually a fermentation broth. The composition is adjusted to the desired pH to dissolve the compound. In some prior art processes, such as the two Merck patents mentioned above, a solvent is added to the composition, in the hope that the compound will dissolve, but the present invention can avoid the need for such solvent addition. As will be appreciated, if one adds a solvent at this stage then it needs to be removed later on in the process. By avoiding the need for a solvent, one can significantly reduce the amount of contaminated waste considerably.

The cells (or the biomass) can be removed by filtration, centrifugation or decantation. Filtering, if used, can be carried out by any method known in the art but is preferably over a rotary vacuum filter or a membrane filter press. The remaining cells (biomass), e.g. in the form of a filter cake can be subsequently washed with water. Preferably it is washed with at least 3 times its volume of water. One then can obtain a solution of the compound which can be a decant, filtrate or supernatant.

After the removal of the cells in (b) the solution can be further basified and/or heated. Thus the pH may be increased, such as to about pH 12. Heating may also be employed. The purpose of this is to convert an unwanted by-product into a useful compound. For example, during fermentation, such as in the production of lovastatin, O-acetyl lovastatin is formed. This by-product can be removed at a later stage, but preferably it can be converted into lovastatin itself, thus increasing the overall yield of this reductase inhibitor. This conversion can be achieved by treating the solution at a high alkaline pH at an elevated temperature.

Thus, the pH of the solution is preferably then adjusted in (a) to from 11 to 13 and/or suitably heated. Preferably heating is to at least 50° C. The duration of heating is dependant on the temperature employed. For example, the solution can be heated for at least 30 minutes (e.g. at about 60° C.) or for at least 10 minutes (e.g. at about 90° C.).

The solution is then contacted with a resin in stage (c) that is adapted to allow the compound to be adsorbed onto it. The solution can be passed over a bed of the resin. This is to concentrate the compound and/or remove polar impurities. The flow rate of the solution can be varied but is preferably from 3 to 6 bed volumes per hour during loading and from 3 to 6 bed volumes at any other time. The resin can be any suitable resin but is preferably a hydrophobic resin, such as a polystyrene resin, for example Amberlite™ XAD-16 or XAD-1180. Preferably up to 40 g of the compound is loaded per liter of resin. However, before this the resin can be conditioned, such as with 1 to 6 bed volumes of aqueous alkali, for example 0.02N NaOH. After adsorption (of the compound) the resin can be washed to remove any impurities which have not been adsorbed. Washing can be carried out using any suitable liquid, for example an acetone-aqueous sodium hydroxide solution, preferably up to 15 %, e.g. from 5 to 15 % acetone in a (e.g. 0.2N) sodium hydroxide solution.

The compound is then removed from the resin, usually by elution. The preferred eluent is a water-miscible solvent, such as an aqueous solvent e.g. comprising water and acetone, or a $C_{1-4}$ alcohol. Suitably the solvent comprises at least 80%, such as at least 60%, acetone: the remainder is preferably water. Following removal of the adsorbed compound, the resin can be regenerated and conditioned for a following cycle by washing. By using a resin the amount of solvent used can be up to 15 times less than for prior art methods.

In a second aspect the invention provides a process (which can follow the process of the first aspect) of purifying or isolating, from an aqueous composition, a compound of general formula I or II, the process comprising:

(a) adjusting, if necessary, the pH of the composition to be less than 7, and optionally adding acetone;

(b) contacting the composition with a water-immiscible solvent comprising toluene so that at least some of the compound is extracted by dissolving in the (toluene-containing) solvent; and (c) optionally, if the compound is of formula I, lactonizing (e.g. in the solvent) the compound to give a compound of formula II.

Preferably the compound is of general formula I: on lactonization it can thus yield a compound of general formula II

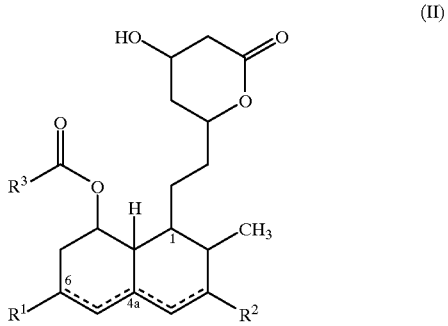

(II)

wherein $R^1$, $R^2$ and $R^3$ are as defined above for formula I and there is one double bond present in the first ring (possessing $R^2$), between either carbon atoms 3 and 4 or atoms 4 and 4a, and no or one double bond in the second ring (possessing $R^1$), which if present is between either carbon atoms 4a and 5 or atoms 5 and 6.

It will be seen therefore that the process of the second aspect can be subsequent to the first aspect. In that event, the aqueous composition is preferably the eluate resulting from stage (d), or removal of the compound (e.g. of formula I), from the resin, of the first aspect.

The aim of the second aspect is to further concentrate the compound. In addition, it can automatically provide the compound in a solvent that is suitable for lactonization. In several prior art processes, a different solvent is used for lactonization than for extraction, and not only does this result in an increase in costs, but it reduces yields.

In addition, the second aspect may result in the removal (by extraction) of undesired polar components, in particular those that are polar at a pH less than 7.

The pH of the composition is preferably adjusted to be from 3 to 5 and most preferably to a pH of about 4. The composition is then contacted with the (toluene-containing) solvent so that the compound is extracted (into the toluene). The amount of toluene added is dependent on the desired concentration of the compound, which can vary from 0.1 g/l to 10 g/l (at room temperature). The duration of contact is not critical, however, preferably the composition is contacted with the solvent for at least 15 minutes.

The solvent comprises toluene because this has been found to give good purification. It can have a high partition coefficient for the precursor. The solvent can contain liquid (s) other than toluene itself. Those other liquid(s) are, however, preferably solvents for the compound as well. Specifically, the invention contemplates the use of acetone in the solvent and hence the solvent preferably comprises toluene and acetone. However, if other liquid(s) are employed, then preferably the toluene is present at least 50%. Alternatively, instead of being present in the solvent, the acetone can be added directly to the composition: in this case it is prefered to have a composition:acetone ratio of from 5:95 to 70:30 (by volume). Whichever way the acetone is added, preferably the ratio (by volume) of toluene:solution is between 1:1 and 5:1. If the process of the second aspect follows the first, then the eluate will already contain some acetone. Lactonization in (c) can then take place, suitably in the same solvent that was used for extraction.

Lactonization of a compound of formula I, to produce a compound of general formula II, can be achieved by heating in the solvent (which can be only toluene). The heating can be from 80° C. to 110° C., e.g. 90° C. to 100° C. (usually under atmospheric pressure). Most of any water or acetone present in the solvent can thus be removed by evaporation at this temperature. Preferably, heating is continued for at least 6 hours. However, heating is preferably not beyond 130° C. as by-products, such as a lovastatin dimer, may be formed.

If the solvent contains acetone, then most of this will have evaporated during the heating process although it is not imperative that all acetone is removed. At preferred conditions, one can obtain a acetone conversion of 98% or higher.

After heating, the solvent is allowed to cool, suitably to room temperature.

Lactonization is an equilibrium reaction: in effect, one is performing ring closure, where the by-product is water which may then evaporate during the heating process.

A third aspect of the invention (which may follow the process of the second aspect) provides a process of purifying (or isolating) compound of general formula II (which may be HMG-CoA reductase inhibitor) from a composition comprising the compound and toluene, the process comprising:

(a) contacting the composition with a (first) aqueous solvent and, if necessary, adjusting the pH to from 8 to 11, optionally followed by removing at least part of the aqueous solvent;

(b) either before or after (a), contacting the (toluene-containing) composition with a (second) aqueous solvent and, if necessary, adjusting the pH to from 2 to 6, and optionally removing at least part of the aqueous solvent; and (c) further purifying, or isolating, the compound from the resulting (toluene-containing) composition.

In effect, therefore, (a) and (b) can be thought of as two extractions each with a respective aqueous solvent, the first at a pH of from 8 to 11 and the second at a pH of from 2 to 6. Although the (alkaline) aqueous wash in (a) has been placed first, in practice they can be interchanged so that (b) is performed first followed by (a).

The process of the third aspect can be subsequent to the process of the second (and additionally the first) aspects. Preferably the compound is one that is to be administered as an inhibitor, and is of the general formula II

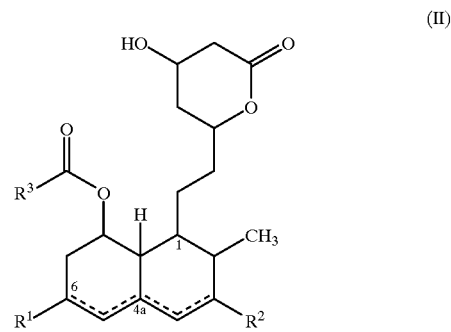

(II)

wherein:
each of $R^1$ and $R^2$ independently represent a hydrogen atom, a methyl group or a hydroxyl group; and $R^3$ represents a (straight chain or branched) $C_{2-6}$ alkyl group;

and there is one double bond present in the first ring, between either carbon atoms 3 and 4 or atoms 4 and 4a, and no or one double bond in the second ring, which if present is between either carbon atoms 4a and 5 or atoms 5 and 6.

Three preferred compounds (all of formula II) have the following formulae:

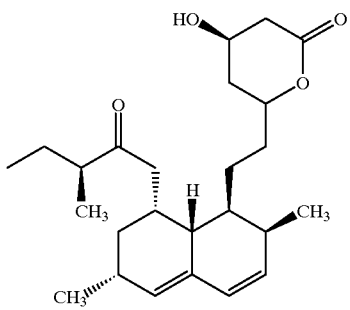

LOVASTATIN

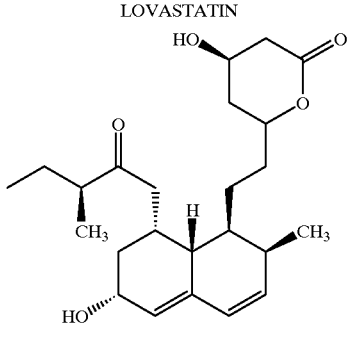

PRAVASTATIN

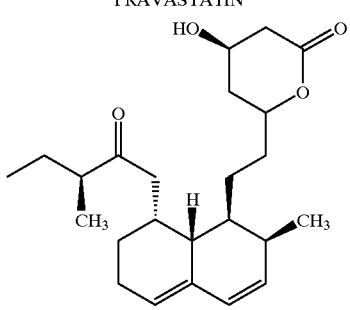

COMPACTIN

Also of formula II is simvastatin which has the same structure as lovastatin except that the 1-methyl propyl side chain is replaced by a 1,1-dimethyl propyl group.

The third aspect can thus involve two (aqueous) washings of the composition containing the toluene and the desired compound. These washings with aqueous solvents can remove undesirable components: thus, unwanted components that are water-soluble, can be extracted into the aqueous solvents. Since the solvents are aqueous, they will not be miscible with the toluene-containing composition.

The toluene-containing composition and aqueous solvent can therefore be mixed, and (the two) phases allowed to separate. In both (a) and (b) at least part (and preferably all) of the aqueous solvent is removed following mixing and/or stirring with the toluene-containing composition.

In stage (a) components with a polar character at a pH from 8 to 11 can be removed, for example any remaining compounds of formula I (such as lovastatin in its acid form). Polar components may remain in the toluene-containing composition following lactonization. Components that remain unconverted as a result of the lactonization process can thereby be removed. Preferably the pH is not above 11, otherwise compounds of formula II may be reconverted back into their open-ringed form (of formula I).

In stages (a) and (b), the aqueous solvent can first be added, before the pH is adjusted, or this performed the other way around. The first is preferred (that is to say, the aqueous solvent is added first, before pH adjustment) otherwise an emulsion can form (of the type water-in-oil such as where the aqueous solvent exists as particles within the toluene-containing composition as the continuous phase).

As will be appreciated, pH adjustment is not necessary if the aqueous solvent is at the correct and desired pH. In (a), this can be achieved by any suitable alkali, for example an alkali metal hydroxide, such as sodium hydroxide (e.g. at about 2N). In (b), any suitable acid can be employed, but it is preferably a mineral acid, such as hydrochloric acid, nitric acid or (preferably) sulphuric acid.

The composition is, in preferred embodiments, contacted with the aqueous solvent in (a) and/or (b) in an amount to give a ratio (by volume) of from 2–3:1 toluene composition:water. The pH in (a) is suitably from 8 to 11, preferably from 9 to 10 and most preferably about 10. The two phases are suitably mixed for from 5 to 60 minutes, preferably from 20 to 40 minutes, and then separated from each other.

A second quantity (e.g. of water) can then be added to (then separated) toluene-containing layer. In (b) the pH is preferably from 2 to 6, such as from 3 to 5 and optimally about 4. The phases are suitably mixed for from 5 to 60 minutes, preferably from 20 to 40 minutes, and then separated from each other.

The compound of formula II can be further isolated and purified by standard techniques known in the art. For example decolorization can be achieved by using activated carbon although one can use any decolorizing agent known in the art. This may remove any coloured and/or hydrophobic components (such as from the resulting toluene-containing composition). Decolorization may be preferred if the reductase inhibitor is of a light colour, for example it is white. However, if the process of the third aspect follows on from the process of the first and second aspects, then the treatment with the resin in (c) of the first aspect may have already removed some of the colouring components.

Crystallization can be carried out using standard techniques and further purification can be achieved by, for example, recrystallisation or chromatography.

A preferred process of the invention, which involves all three aspects, therefore comprises a process for preparing a compound of formula I or II:

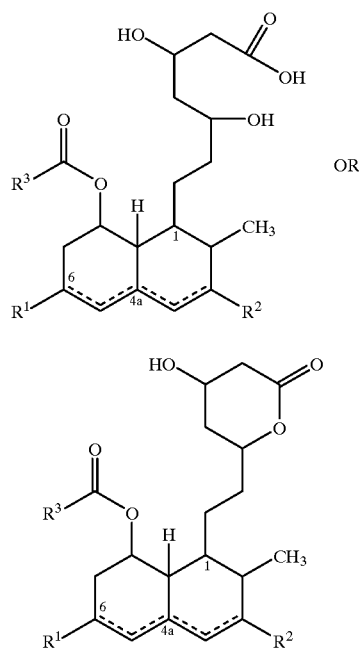

wherein:

each of $R^1$ and $R^2$ independently represents a hydrogen atom, a methyl group or a hydroxyl group; and $R^3$ represents a (straight chain or branched) $C_{2-6}$ alkyl group;

or a salt or isomer thereof;

and there is one double bond present in the first ring, between either carbon atoms 3 and 4 or atoms 4 and 4a, and no or one double bond in the second ring, which if present is between either carbon atoms 4a and 5 or atoms 5 and 6;

the process comprising:

providing a composition comprising cells that have produced compound of formula I or II; and (1) adjusting, if necessary, the pH of the composition to be at least 7.5;

(2) removing the cells from the composition to obtain a solution of the compound;

(3) optionally heating the solution;

(4) contacting the solution with a resin so that the compound is adsorbed onto the resin, removing the compound from the resin into an aqueous composition arid, if necessary adjusting the pH of the composition to be less than 7;

(5) contacting the composition with a water-immiscible solvent comprising toluene, so that at least some of the compound is extracted by dissolving in the (toluene-containing) solvent;

(6) if the compound is of formula I, optionally lactonizing the compound in the solvent to produce a compound of formula II;

(7) contacting the resulting composition comprising the compound and toluene with a (first) aqueous solvent and, if necessary, adjusting the pH to be from 8 to 11, and optionally removing at least part of the aqueous solvent;

(8) either before or after stage (7), contacting the (toluene-containing) composition with a (second) aqueous solvent and, if necessary, adjusting the pH to from 2 to 6, and optionally removing at least part of the aqueous solvent;

(9) optionally decolorizing the resulting (toluene-containing) composition;

(10) optionally performing crystallization and/or drying, and if desired further purifying the compound.

As will be appreciated, the preferred features and characteristics for the first, second and third aspects can be incorporated into the protocol outlined in the previous paragraph.

One advantage of the process according to the present invention compared to prior art extraction processes can be that the use of a resin (for adsorption/desorption) can reduce the amount of solvent required. The yield of compound obtained can be high, despite the number of steps involved in the process. It should be borne in mind that as the three aspects (processes) of the invention can be performed, in that order, as part of or to form a larger multi-stage process, preferred features of one aspect, where applicable, are valid for another aspect mutatis mutandis.

The following examples are provided to illustrate and in no way limit the scope of the process of the present invention and should not be construed as being limiting.

Comparative Example 1

Production of Lovastatin Containing Fermentation Broth of *Aspergillus Terreus*

*Aspergillus terreus* strain AD43, DS number 28373 has been deposited with the Centraal Bureau voor Schimmel-cultures (CBS, Delft, The Netherlands) and has been granted CBS accession number CBS 456.95.

One 1 ml vial of a spore suspension of *Aspergillus terreus* strain AD43, stored in glycerol at −80° C. was opened aseptically, and contents were suspended in a 2 liter shake flask containing 500 ml of the following medium (heated in an autoclave for 20 minutes at 121° C.).

| Ingredient | Amount per kg |
|---|---|
| Glucose.1H$_2$O | 10 g |
| Oatmeal | 10 g |
| Tomato paste | 40 g |
| Corn steep liquor | 5 g |
| Trace elements | 1 g |

The composition of the trace element solution (per 100 ml of distilled water) was: FeSO$_4$.7H$_2$O, 1 g; MnSO$_4$.1H$_2$O, 1 g; CuCl$_2$.2H$_2$O, 0.025 g; CaCl$_2$.2H$_2$O, 0.1 g; H$_3$BO$_4$, 0.056 g; (NH$_4$)$_6$Mo$_7$O$_{24}$.4H$_2$O, 0.019 g; ZnSO$_4$.7H$_2$O, 0.2 g.

The shake flasks were incubated at 28° C. for 24 hours in a rotary shaker at 280 rpm (throw of 3.5 cm). Eight flasks were used for inoculation of one fermenter with 2000 kg of broth weight. The composition of the fermentation broth was as follows:

| Ingredient | Amount per kg |
|---|---|
| Glucose.1H$_2$O | 22 g |
| Yeast extract paste | 33 g |
| Polypropylene glycol 2000 | 2.5 ml |

Before sterilisation the pH of the solution was decreased to pH 4.5 with sulphuric acid. Sterilisation was performed for 45 minutes at 121° C. Fermentation conditions were as follows: pH was kept constant at 6.5 using H$_2$SO$_4$ and NaOH; temperature was 28° C.; dissolved oxygen concentration was kept at 20% by stirring speed, overpressure and air supply. Minimum values were respectively: 150 rpm, 0.2 bar and 155 kg of air per hour.

As soon as all the glucose was consumed a glucose/yeast extract feed was started at a rate of 1.2 g of glucose per kg of broth per hour. The composition of the feed was:

| Ingredient | Amount per kg |
|---|---|
| Glucose.1H$_2$O | 550 g |
| Yeast extract paste | 17 g |
| Polypropylene glycol 2000 | 14 ml |

After 192 hours this fermentation yielded 750 mg lovastatin per liter.

EXAMPLE 2
Isolation of Crude Lovastatin Crystals Via Extraction of Broth Filtrate The pH of 1.8 L of broth of strain AD43, produced according to Example 1, was adjusted to pH 10. After half an hour the broth was filtered and the filter cake was washed with three cake volumes of water, resulting in 3 L of broth filtrate with a lovastatin acid concentration 0.40 g/l.

The pH of the filtrate was brought to pH 12.5 with 2 N NaOH at 25° C., and subsequently heated at 50° C. for 2 hours. After 2 hours the reaction was complete, and the reaction mixture cooled to room temperature. The pH was lowered to pH 4 using sulphuric acid and 9 L of toluene were added and mixed over 30 minutes. The toluene layer was separated from the water layer and subsequently concentrated to a volume of 250 ml by evaporation at 40° C. under vacuum to give a lovastatin (acid) concentration of 4.3 g/l.

The lovastatin acid in the extract was converted into the lactone by heating it to 90° C. for 3 hours (yield of conversion was 99.2%). After cooling to room temperature, the toluene was mixed with 250 ml of water, while the pH was adjusted to pH 10 with NaOH. After separation of the layers, the toluene layer was mixed again with 250 ml of fresh water, while the pH is adjusted to pH 4 with sulphuric acid. After separation of the layers, the toluene layer was treated with 0.3 g of activated carbon, Norit SX Ultra™.

Subsequently the toluene solution was filtered and further concentrated to 15 ml by evaporation. Cooling to –10° C. resulted in crystallization. The crystals were washed with 5 ml of cold toluene, and dried under vacuum at room temperature, yielding 0.83 g of crude lovastatin crystals with a purity of 90.7% (HPLC).

EXAMPLE 3
Isolation of Lovastatin from Fermentation Broth Via Extraction of Broth Filtrate Two fermentations of 2.5 m$^3$ each, as performed in Example 1, were combined. The pH was brought to pH 10 with 2 N NaOH and stirred for 0.5 hr. The broth was filtered over a membrane filter press, yielding 3100 L of filtrate with 0.54 g of lovastatin.

2100 L of broth filtrate was extracted in three subsequent portions of 700 L each with 2100 L of toluene, in order to obtain a good phase separation. The overall extraction yield was 90%. The extract was concentrated by evaporation of toluene to a lovastatin (acid) concentration of 5 g/l (final volume 200 L), and then the lovastatin acid in the extract lactonized by heating the solution at 90° C. for 6 hr (to give a conversion of 97.6%).

After cooling to room temperature, 200 L of water was added, whereafter the pH was adjusted to pH 10 with 2 N NaOH. After 0.5 hr the phases were separated, and another 200 L of water added to the toluene phase, whereafter the pH was adjusted to pH 4 with 2N H$_2$SO$_4$. After 0.5 hr mixing, the phases were allowed to settle and separate. Then 300 g of active carbon Norit SX-Ultra™ was added to the toluene layer, mixed for 1 hour and filtered.

The toluene phase was further concentrated to a lovastatin concentration of 60 g/l by evaporation of toluene at 70° C. under reduced pressure. Then the toluene phase was slowly cooled at a rate of 0.25° C./min to –10° C. The crystals were filtered, washed with 3 L of cold toluene (–10° C.) and dried at room temperature under vacuum, yielding 760 g of crude lovastatin crystals with a purity of 93.5% (HPLC).

EXAMPLE 4
Isolation of Crude Lovastatin Crystals Using Hydrophobic Adsorption of Lovastatin Acid from Broth Filtrate The pH of 15 L of broth of strain AD43, which was produced according to Example 1, was adjusted to pH 10 with 2N NaOH. After 30 minutes stirring at pH 10, the broth was filtered, and the filter cake was washed with 3 cake volumes of water. The filtrate (lovastatin acid concentration 0.40 g/l) was brought to pH 12.5 with 2N NaOH at 25° C., and subsequently heated at 60° C. for 30 min. After 30 minutes the reaction was complete, and the reaction mixture was cooled to room temperature and filtered, resulting in 25 L of broth filtrate with a lovastatin acid concentration of 0.43 g/l.

A column was prepared with 300 ml of the hydrophobic resin XAD-16™. Prior to loading the filtrate onto the column, the resin was conditioned with 0.02 N NaOH. Subsequently, the pH of the filtrate was adjusted to pH 12, and lovastatin acid adsorbed onto the hydrophobic resin XAD-16 by leading 25 L of the heat-treated filtrate over the column. The column was washed with 3 bedvolumes of 0.2 N NaOH. Lovastatin acid was subsequently eluted from the resin with 3 bedvolumes of a mixture of 70% acetone in water. The concentration of lovastatin acid in the eluate was 11 g/l.

Subsequently, the eluate was extracted with 2 L of toluene at pH 4. After phase separation, acetone and water were evaporated at a temperature of 110° C., the toluene-solution was then kept at temperatures between 90° C. and 110° C. to induce lactonization. After 6 hours of reaction time, 98% of lovastatin acid was converted into lovastatin. The solution was cooled to room temperature and washed with water by adding 1 L of water to the toluene. The pH was adjusted to pH 10 with 2 N NaOH. The phases were separated, and the washing procedure repeated once more. Afterwards, 1 L of water was again added to the toluene phase, and the pH adjusted to pH 4 with 2 N H$_2$SO$_4$. After separation of the phases, 7 g of Norit SX-Ultra™ was added, and stirred for 1 hour before filtration.

The toluene was then evaporated to obtain a lovastatin concentration of 60 g/l. The solution was cooled at a rate of 0.5° C./min to –10° C., yielding 7.4 g of crude lovastatin crystals with a purity of 92.2%.

EXAMPLE 5
Isolation of Lovastatin Acid Via Hydrophobic Adsorption of Lovastatin Acid from Broth Filtrate To 2.5 m$^3$ of broth of strain AD43, produced according to Example 1, 1250 L of water was added. Subsequently the pH of the diluted broth was adjusted to pH 10 with 2 N NaOH. After 30 minutes stirring at pH 10, the broth was filtered, yielding 3 m$^3$ of filtrate with a lovastatin acid concentration of 0.44 g/l. Subsequently the pH of the filtrate was brought to pH 12.5 with 2 N NaOH at 25° C., and then was heated at 60° C. for 30 min. After 30 minutes, the reaction was completed, and the reaction mixture was cooled to room temperature and filtered, resulting in 3 m³ of broth filtrate with a lovastatin acid concentration of 0.47 g/l.

A column was prepared with 20 L of the hydrophobic resin XAD-16™. Prior to loading the filtrate onto the column, the resin was conditioned with 0.02 N NaOH. Subsequently, the pH of the filtrate was adjusted to pH 12, and lovastatin acid was adsorbed onto the hydrophobic resin XAD-16 by leading 1.5 m³ of the heat-treated filtrate over the column. The column was washed with 3 bedvolumes of 0.2 N NaOH. Lovastatin acid was subsequently eluted from the resin with 3 bedvolumes of a mixture of 70% acetone in water. The concentration of lovastatin acid in the eluate was 11.5 g/l.

Subsequently, the eluate was extracted with 140 L of toluene at pH 4. After phase separation, acetone and water were evaporated at a temperature of 110° C., the toluene-solution (lovastatin content 4.7 g/1) was then kept at temperatures between 90° C. and 110° C. to induce lactonization. After 6 hours of reaction time, 99% of lovastatin acid was converted into lovastatin. The solution was then cooled to room temperature and washed with water by adding 70 L of water to the toluene. The pH was adjusted to pH 10 with 2 N NaOH. The phases were separated, and the washing procedure repeated once more. Again 70 L of water was added to the toluene phase, and the pH adjusted to pH 4 with 2 N H₂SO₄. After separation of the phases, 200 g of Norit SX-Ultra™ was added, and stirred for 1 hour before filtration.

The toluene was then evaporated to obtain a lovastatin concentration of 60 g/l. The solution was cooled at a rate of 0.25° C./min to −5° C., yielding 530 g of crude lovastatin crystals with a purity of 95.5% (HPLC).

EXAMPLES 6 & 7

Comparison of the Extraction of Lovastatin from Broth Filtrate with Toulene with and without the Presence of Acetone The pH of 100 ml of a broth filtrate, obtained from the fermentation broth of Example 1, containing 1 g/l of lovastatin was adjusted to pH 4 with sulphuric acid. The broth filtrate was mixed with an equal amount of toluene, and stirred for 15 minutes. After separation of the emulsion by centrifugation, the toluene phase (93 ml) had a lovastatin content of 0.6 g/l, which is a yield of 58% (Example 6).

The pH of another 100 ml of the same fermentation broth filtrate was also adjusted to pH 4 with sulphuric acid. Then (Example 7) a mixture of 85 ml of toluene and 15 ml of acetone were mixed with the broth over a period of 15 minutes. After separation, the toluene layer (99 ml) had a lovastatin content of 1.13 g/l, a yield of 100%.

What is claimed is:

1. A process for recovering from a fermentation broth a compound having formula I or II:

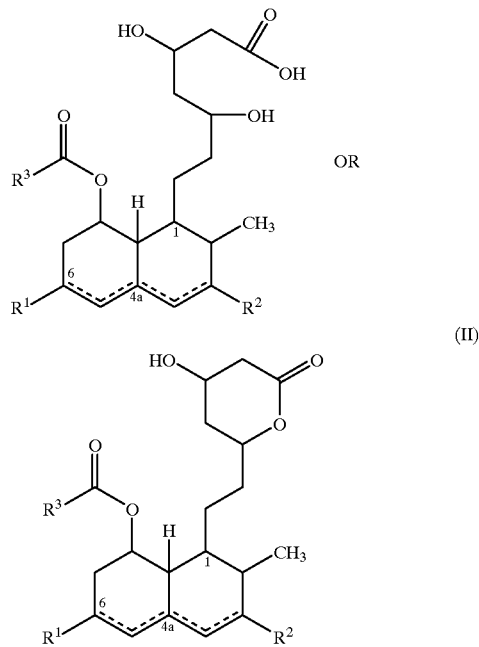

or a salt or isomer thereof;
wherein:
each of $R^1$ and $R^2$ independently represents a hydrogen atom, a methyl group or a hydroxyl group; and
$R^3$ represents a $C_{2-6}$ alkyl group; and there is one double bond in the first ring between either carbon atoms 3 and 4 or 4 and 4a, and no or one double bond in the second ring between either carbon atoms 4a and 5 or 5 and 6;
the process consisting essentially of:
(1) adjusting the pH of the fermentaion broth to be at least 7.5 therby solubilizing any compound from the cells;
(2) removing the cells from the pH-adjusted fermentation broth to obtain a solution of the compound;
(3) heating and/or adjusting the pH of the solution to convert unwanted byproduct into said compound;
(4) contacting the solution of step (4) with a resin to absorb the compound onto the resin, eluting the compound from the resin into forming an aqueous composition and, if necessary adjusting the pH of the composition to be less than 7;
(5) contacting the aqueous composition with a water-immiscible solvent comprising toluene to extract the compound;
(6) lactonizing any compound having formula I in the extract solvent to form compound having the formula II;
(7) contacting the extract solvent comprising the compound and toluene with a first aqueous solvent and, if necessary, adjusting the pH to be from 8 to 11, and optionally removing at least part of the aqueous solvent;
(8) either before or after stage (7), contacting the toluene-extract solvent with a second aqueous solvent and, if necessary, adjusting the pH to from 2 to 6, and optionally removing at least part of the aqueous solvent;
(9) decolorizing the resulting toluene-containing extract-solvent; and

(10) recovering the compound through crystallization and/or drying the compound.

2. A process according to claim 1 wherein in step (1) the pH of fermentation broth containg the cells is adjusted to a pH of from 9 to 13 and the resin in step (4) is hydrophobic.

3. A process according to claim 1 wherein in step (4) the compound is removed from the resin by elution with a water-miscible solvent comprising acetone and the resin is a polystyrene resin.

4. A process according to claim 1 wherein in step (4) the pH of the aqueous composition is adjusted to from 3 to 5 and the solvent in step (5) comprises toluene and acetone.

5. A process according to claim 1 wherein in step (6) the compound having formula (1) is lactonized by heating at from 80° C. to 120° C., optionally directly in the solvent from step (5).

6. A process according to claim 1 wherein the pH in step (7) is from 9 to 10 and the pH in step (8) is from 3 to 5.

7. A process according to claim 1, wherein the compound is lovastatin, pravastatin or compactin.

8. A process of purifying from a fermentaiton broth containing cells that produced a compound of the general formula I or II:

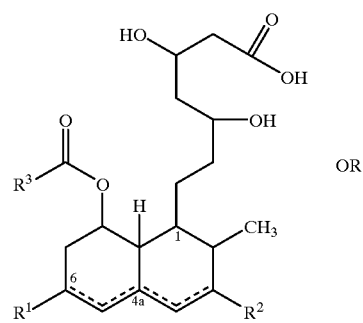

(I)

OR

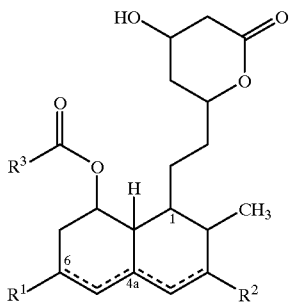

(II)

or a salt or isomer thereof;
wherein:

each of $R^1$ and $R^2$ independently represents a hydrogen atom, a methyl group or a hydroxyl group; and $R^3$ represents a $C_{2-6}$ alkyl group; and there is one double bond present in the first ring, between either carbon atoms 3 and 4 or 4 and 4a, and no or one double bond in the second ring, which if present, is between either carbon atoms 4a and 5 or 5 and 6; the process consisting essentially of:

(a) adjusting the pH of the fermentaiotn broth containing the cells with an akali so that the broth is at least 7.5 therby solubilizing any compound from the cells;

(b) removing the cells from the fermentation broth to obtain a solution of the compound;

(c) contacting the solution with a resin to absorb the compound onto the resin; and (d) removing the compound from the resin.

9. A process according to claim 8 wherein the compound is lovastatin, pravastatin or compactin.

* * * * *

UNITED STATES PATENT AND TRADEMARK OFFICE
CERTIFICATE OF CORRECTION

PATENT NO.    : 6,268,186 B1  
DATED         : July 31, 2001  
INVENTOR(S)   : Mieke Sibeijn et al.

It is certified that error appears in the above-identified patent and that said Letters Patent is hereby corrected as shown below:

<u>Title page,</u>  
Item [73], Assignee, delete "DSM N.V., Te Heerlen (NL)" and insert -- Plus Chemicals B.V. Mijkrecht (NL) --

Signed and Sealed this

Third Day of June, 2003

JAMES E. ROGAN  
*Director of the United States Patent and Trademark Office*